United States Patent [19]

Baum

[11] Patent Number: 4,929,238

[45] Date of Patent: May 29, 1990

[54] MULTI-PRESSURE INJECTOR DEVICE

[75] Inventor: Thomas M. Baum, Raleigh, N.C.

[73] Assignee: Coeur Laboratories, Inc., Raleigh, N.C.

[21] Appl. No.: 275,272

[22] Filed: Nov. 23, 1988

[51] Int. Cl.⁵ .............................................. A61M 5/00
[52] U.S. Cl. .................................... 604/208; 604/118; 604/218
[58] Field of Search ............... 604/208, 209, 210, 118, 604/121, 123, 124, 218, 227, 191, 100

[56] References Cited

U.S. PATENT DOCUMENTS

| | | |
|---|---|---|
| 984,037 | 2/1914 | Sheets . |
| 1,234,582 | 6/1917 | Trueblood . |
| 1,707,880 | 4/1929 | Sheets . |
| 1,950,137 | 3/1934 | Dowe ................................... 123/214 |
| 2,939,459 | 6/1960 | Lazarte et al. . |
| 3,749,084 | 7/1973 | Cucchiara . |
| 3,957,051 | 5/1976 | Topham ........................... 604/191 X |
| 3,985,122 | 10/1912 | Topham . |
| 4,116,240 | 9/1978 | Guiney . |
| 4,188,949 | 2/1980 | Antoshkiw . |
| 4,214,584 | 7/1980 | Smirnov et al. . |
| 4,254,773 | 3/1981 | Waldbillig ............................ 128/348 |
| 4,313,440 | 2/1982 | Ashley . |
| 4,439,184 | 3/1984 | Wheeler ................................ 604/191 |
| 4,452,473 | 6/1984 | Ruschke ............................... 285/332 |
| 4,583,978 | 4/1986 | Porat et al. ........................... 604/208 |
| 4,629,455 | 12/1916 | Kanno ................................... 604/241 |
| 4,655,747 | 4/1987 | Allen, Jr. .............................. 604/191 |
| 4,702,737 | 10/1927 | Pizzino ................................. 604/191 |
| 4,758,223 | 7/1988 | Rydell .................................. 604/100 |
| 4,759,750 | 7/1988 | DeVries et al. ...................... 604/121 |

Primary Examiner—John D. Yasko
Attorney, Agent, or Firm—Steven J. Hultquist

[57] ABSTRACT

A multi-pressure injector device, having utility as an angiographic syringe or as an inflation device for balloon angioplasty, wherein an inner barrel/plunger is reposed slidably reposed in an outer barrel, with a second plunger slidably reposed in the inner barrel/plunger, and with the inner barrel/plunger and outer barrel being selectively longitudinally lockable relative to one another along the length of travel of the inner barrel/plunger in the outer barrel. A quick-lock/release structure is disclosed, which is particularly suitable for use with inflation devices for balloon angioplasty. In one aspect, the injector comprises a rotatable connector which is mounted at a distal end of the injector, and includes a distal threaded neck portion and a proximal collar portion of greater diameter than the injector barrel. Such rotatable connector construction facilitates ease of use in attaching the injector to complementary matable structure of catheters, manifolds, and other fluid delivery means.

26 Claims, 7 Drawing Sheets

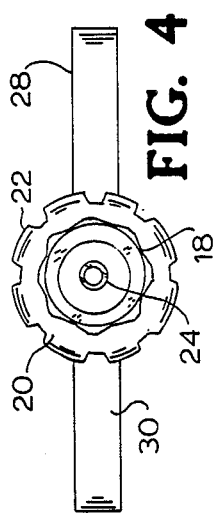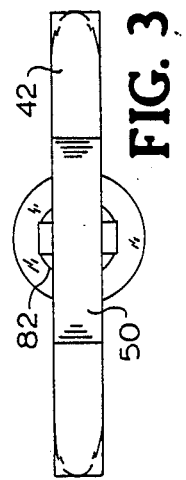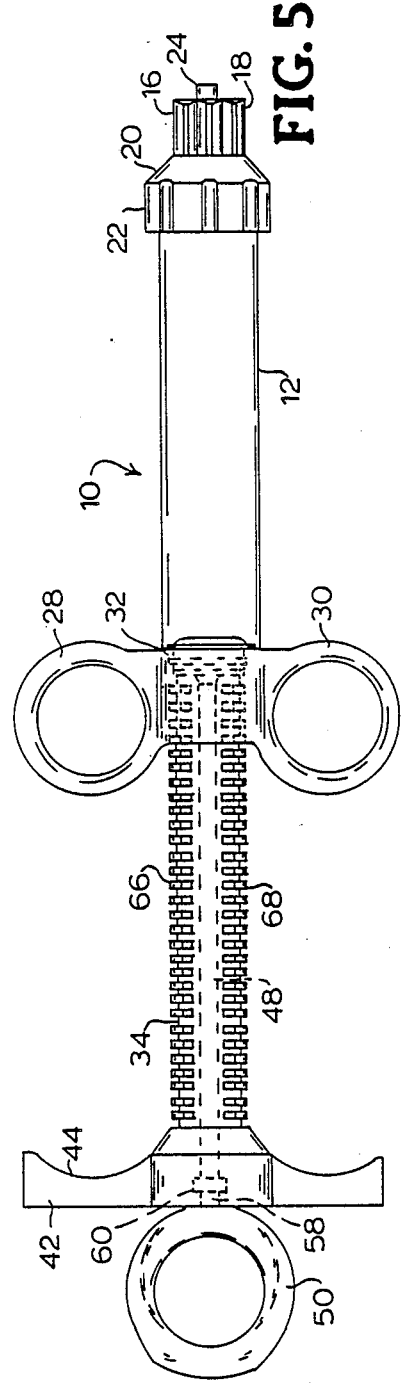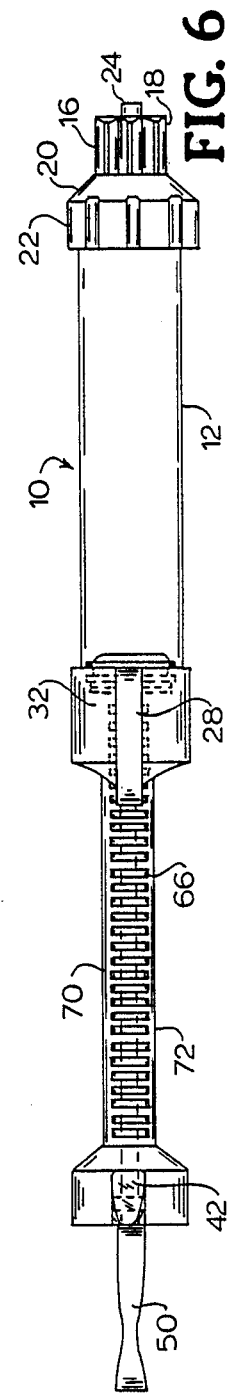

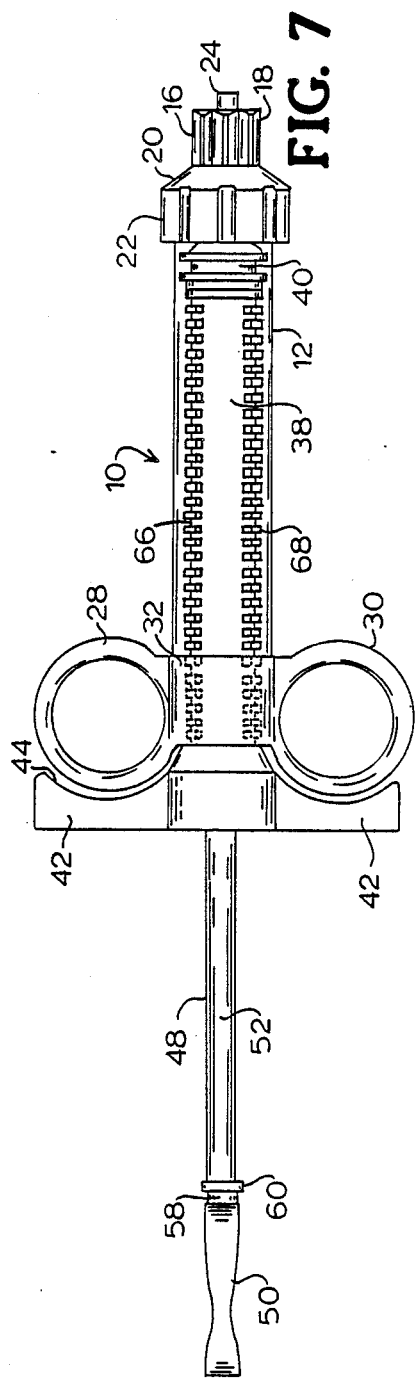
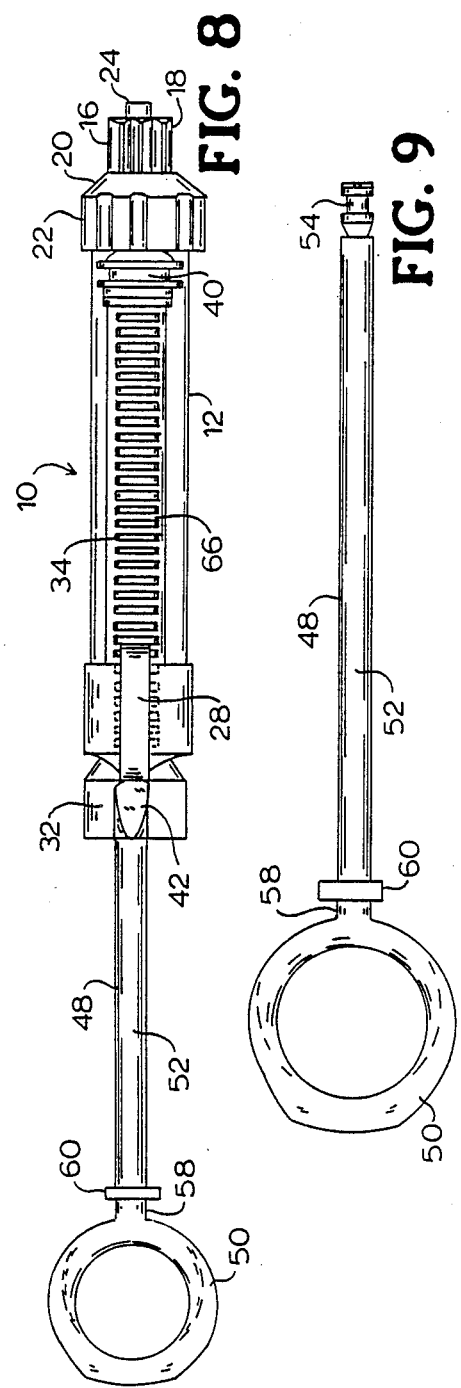

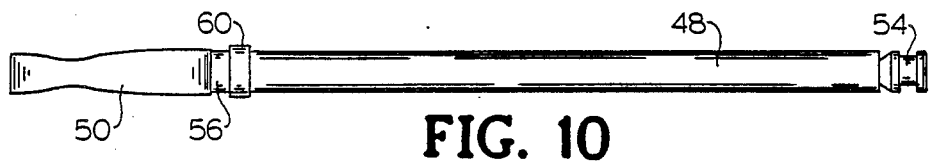
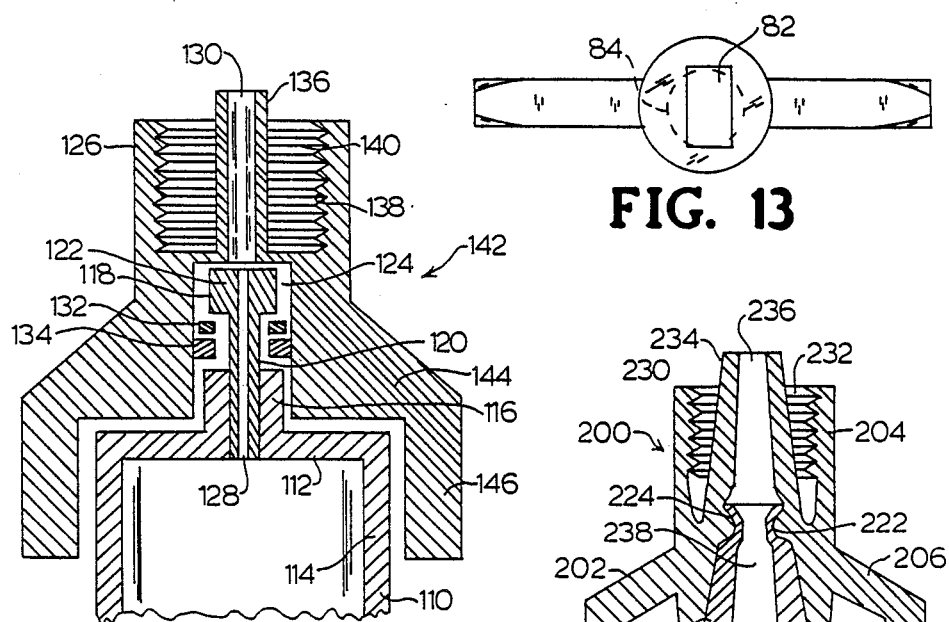
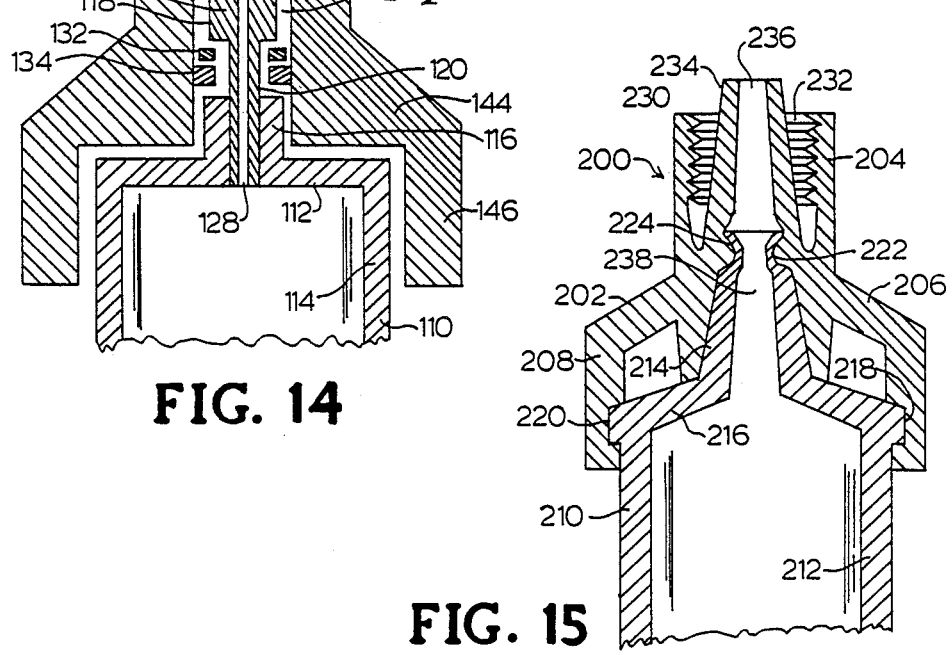
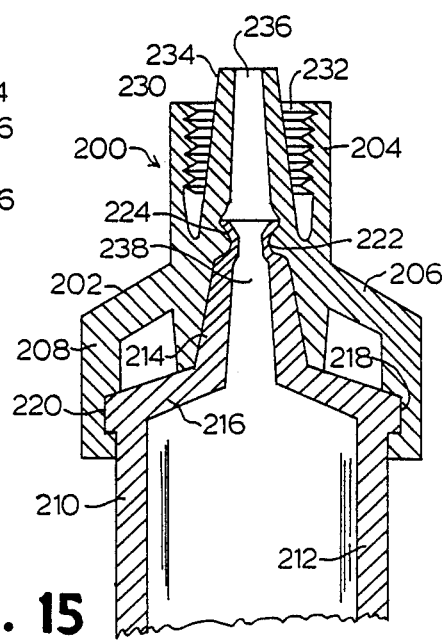

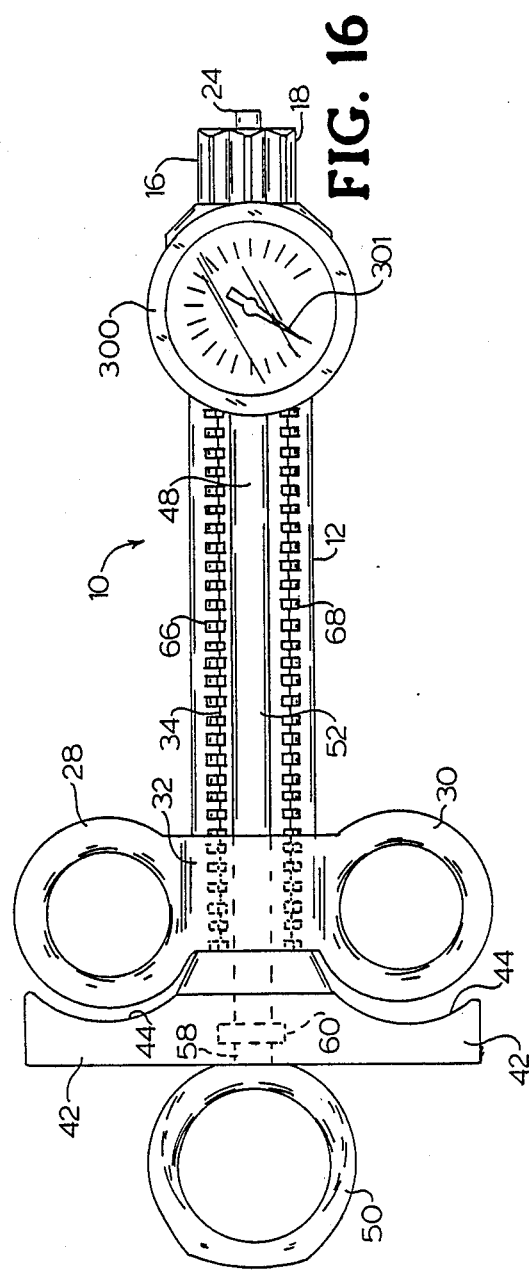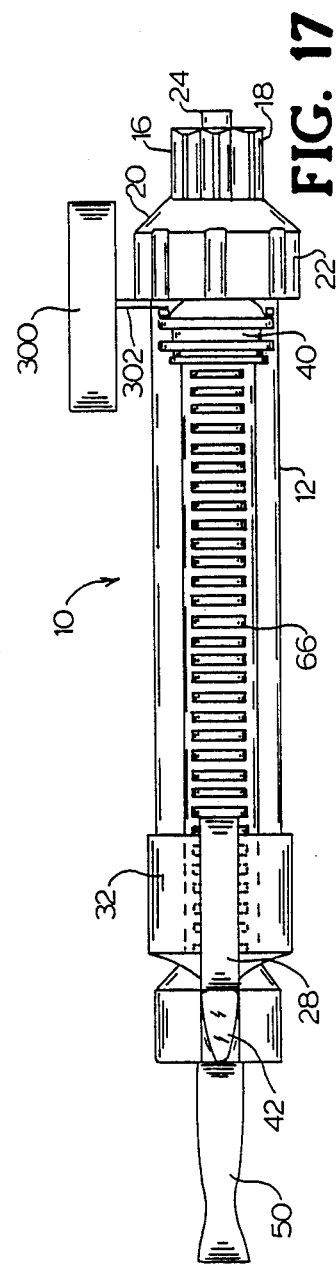

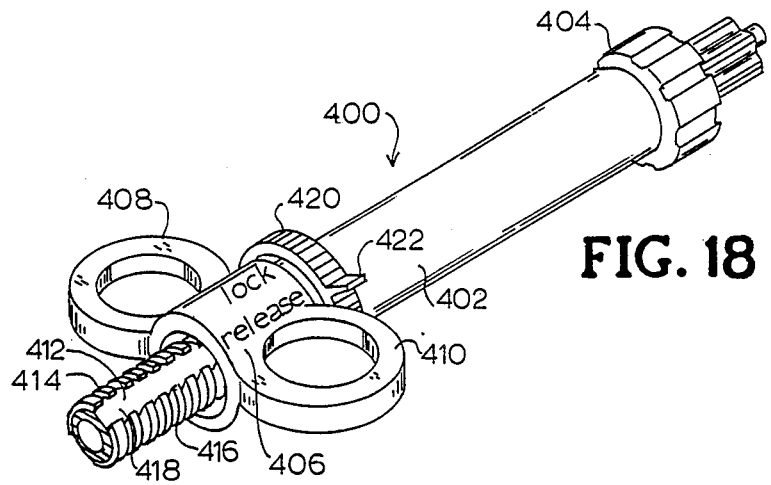
FIG. 18
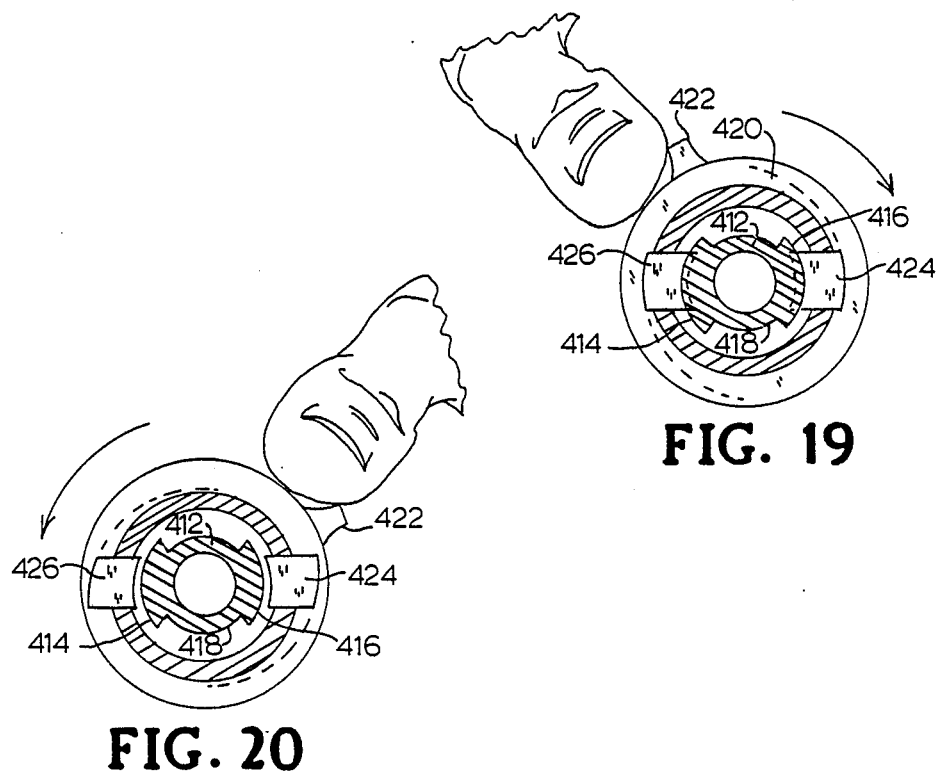
FIG. 19
FIG. 20

MULTI-PRESSURE INJECTOR DEVICE

BACKGROUND OF THE INVENTION

1. Field of the Invention

This invention generally relates to an injector having utility in angiography and/or angioplasty applications, and capable of delivering fluid at multiple selected pressures.

2. Description of The Related Art

In the field of angiography, a contrast medium such as iodine or other fluid of suitable indicating character (radiopacity) is introduced under pressure into coronary arteries, and the arterial network then is monitored by fluoroscopic or other visualizing means. As a result, arterial plaque deposits and/or other arterial occlusions are readily visually determined as to their size and location, so that suitable treatment methods, such as removal of the occluding material by lasing or mechanical excision, or displacement techniques such as balloon angioplasty, may be carried out.

To effect the introduction of the contrast medium into the arterial network for angiographic study, it has been common practice to utilize injector syringes in combination with arterial catheters. The syringe may be hand-held, or machine mounted, and is connected at its distal end to the catheter which is introduced into the arterial system to be studied.

In the angiography procedure, the arterial catheter attached to the injector syringe is typically introduced into the femoral artery and subsequently translated in the arterial passage toward the heart. During this "threading" procedure through the arterial network, it frequently is desirable to inject small volumes of the contrast medium from the syringe into the catheter for discharge at the distal end of the catheter, in order that radiographic detection of the catheter distal end may be achieved, and the arterial catheter may be properly directed to the desired arterial locus.

Thus, small volumes of the contrast medium are injected for guidance, and it is desired to minimize the actual volume discharged at the distal end of the catheter, in order to precisely locate the catheter's distal end, as well as to avoid undue introduction of excessive amounts of the contrast media into the vascular network, such as may be deleterious to the subject being catheterized. Accordingly, close control of the injection of such "guidance volumes" is required.

Further, when small volume blood vessels are present in the arterial network to be studied, either of intrinsically small size, or of reduced diameter due to conditions such as atherosclerosis, relatively smaller volumes of the contrast medium are employed, and higher pressure injection is necessary.

Thus, in the broad practice of angiography utilizing injector syringes and associated arterial catheters, situations are encountered requiring widely divergent pressure levels and volumes of introduced medium. Unfortunately, the injector syringes heretofore employed in angiographic applications do not possess any capability for varying the pressure level of the introduced contrast medium.

Apart from the foregoing, syringes have also been employed as fluid delivery devices in balloon angioplasty applications, in which a ballon catheter having a deflated balloon at its distal end is introduced into an artery for translation therein to the site of arterial blockage, e.g., plaque deposit, and a syringe device at the proximal end of the balloon catheter is employed to introduce fluid into the balloon to expand same, thereby displacing the arterial occlusion and enlarging the cross-sectional flow area in the artery at the previously occluded site. After the balloon has been inflated to a predetermined or selected extent, typically involving pressures of up to about 300 psi, or to even higher pressures, the pressure on the balloon is released, typically by a "quick-release" lever mounted on, or associated with, the inflation syringe ("endoflator").

In balloon angioplasty applications, precise control of the inflation pressure level is critical to achieving the desired de-occlusion of the arterial passage being treated. Further, there is a degree of "art" involved in the angioplasty procedure, in that the thoracic surgeon or other individual doing the balloon angioplasty procedure typically adjusts the balloon pressure to a predetermined set value in the vicinity of that anticipated to be required to adequately inflate the balloon, followed by some additional "fine tuning" adjustment to get the proper "feel" of fluid pressure resistance on the plunger of the inflation syringe, indicative of an effective level of inflation being achieved in the balloon.

Presently, there is an extensive and increasing use of hand-held syringes of various sizes, as well as machine-assisted syringes, in the medical technology field, for injecting fluids into catheter balloons, blood vessls, and other physiological loci. Such injection is typically done under elevated pressure conditions, and must be carried out in a highly accurate manner in terms of introduced fluid volumes and pressure levels. Consistent with a trend toward higher injection pressures, and to better enable the syringe operator to exert effective pressures on hand-held syringes, the medical products industry has evolved syringes having sturdier finger and thumb grips, so that higher pressure levels can be manually applied, relative to hand-held syringes previously in use.

Thus, there is a continuing need in the art to provide syringes having a flexible character for providing moderate presssure injection levels, as for example on the order of up to about 100 psi, as well as higher injection pressures, e.g., up to about 1,000 psi and above, in the case of power injector systems.

U.S. Pat. No. 984,037 to J. H. Sheets discloses a syringe comprising a ported hollow piston rod, having a port at the distal end of the rod as well as a proximal port open to the exterior environment. Such arrangement allows liquid to flow through an open passage in the piston, and to flow proximally of the piston, or distally thereof, as desired. See also the vial syringe disclosed in J. H. Sheets' U.S. Pat. No. 1,707,880, representing an improvement over his earlier patented syringe.

U.S. Pat. No. 1,950,137 to F. Le C. Dowe describes a double-barreled, double-plunger syringe, in which the distal end of the syringe is formed with separate passages communicating with the respective inner and outer barrels, depending on the relative position therebetween. A piston is provided in the outer barrel, attached to finger grips which are vertically adjustable in a corresponding track. The finger grips are attached to a spring, and the track has a saw tooth surface for ratchet action retention of the piston in a desired position. By this construction, the inner barrel is said to be selectively rotatable so that blood may be withdrawn from varicose veins and treatment solution injected without removing the syringe or changing its position, and without the withdrawn blood and the treatment solution coming in contact with one another.

U.S. Pat. No. 1,234,582 to B. T. Trueblood discloses a sequential injection hypodermic syringe, in which a first material in an outer barrel of the syringe is injected by forwardly advancing the inner barrel, and then a second substance contained in the inner barrel is injected by forwardly advancing a plunger resposed in the inner barrel.

A tandem syringe is described in U.S. Pat. No. 2,939,459 to J. A. Lazarte, et al in which the inner barrel of a two-barrel syringe is provided on its anterior face with a puncturable resilient diaphragm, so that a syringe needle extending into the interior of the outer barrel is able to pierce the diaphragm. The inner barrel is fillable with a first volume of a solution, and the diaphragm is of a self-resealable character, so that when the inner barrel is proximally withdrawn from the distal end, a second volume of solution may be introduced into the outer barrel.

Other sequential filling/dispensing syringe constructions having multiple barrel or plunger structures include U.S. Pat. No. 3,749,084 to A. L. Cucchiara; U.S. Pat. No. 4,188,949 to W. T. Antoshkiw; U.S. Pat. No. 4,313,440 to S. J. Ashley; and U.S. Pat. No. 4,702,737 to J. L. Pizzino.

Single barrel compartmentalized syringes are also known, such as the mixing syringe of U.S. Pat. No. 4,116,240 to A. C. Guiney, and various single barrel syringes have been developed containing free floating barriers for forming separate chambers in the barrel, such as U.S. Pat. No. 3,985,122 to S. C. Topham; U.S. Pat. No. 4,044,758 to B. C. Patel; and U.S. Pat. No. 4,439,184 to R. P. Wheeler.

Other multiple-chambered injection apparatus are disclosed in U.S. Pat. No. 4,214,584 to B. A. Smirnov, et al and U.S. Pat. No. 4,655,747 to R. E. Allen, Jr.

With respect to the distal coupling means of the syringe of the present invention, leur connector devices are disclosed in U.S. Pat. No. 4,452,473 to R. R. Ruschke, and U.S. Pat. No. 4,629,455 to M. Kanno. A two-piece swivel coupling for a catheter system having luer connections on either end of the coupling is disclosed in U.S. Pat. No. 4,254,773 to C. C. Waldbillig.

U.S. Pat. No. 4,758,223 to M. A. Rydell discloses a hand-operated inflator for balloon-type catheters, including first and second coaxially disposed plunger operated pistons within a tubular syringe housing comprising a first, relatively large diameter tubular syringe portion and an integrally joined second tubular syringe portion of lesser diameter. The angioplasty catheter is filled by forcing the contents of the larger diameter syringe portion through the catheter by depressing the first plunger coupled to the large diameter piston. After the catheter has been filled in such manner, the pressure in the dilation expander member is adjusted by manipulating the piston cooperating with the smaller diameter syringe portion. The patent states that by incorporating the two syringes in the same housing, a large volume of fluid such as a radiopaque contrast medium can be injected through the catheter and out its distal end, while the small diameter and volume syringe can be used to pressurize the expander with considerably less effort than if the large diameter syringe alone had been used.

The Rydell patent at column 6, lines 45–49 thereof, discloses an illustrative embodiment wherein the larger diameter syringe portion has a volume of approximately 10 cc. and the smaller diameter portion has a volume of approximately 2 cc. In the embodiment of the invention shown in FIG. 4 of this patent, the smaller diameter piston is attached to a knob by means of a pin which is longitudinally movable in a corresponding slot in the outer plunger. In this manner, the inflator operator can force the smaller piston into a correspondingly dimensioned distal passage in the outer barrel of the syringe.

In an alternative embodiment shown in FIGS. 6 and 7 of the Rydell patent, a freely rotatable sleeve is mounted on the outer piston and joined by means of a corresponding lateral pin to the inner piston. The pin joined to the inner piston is longitudinally translatable in a corresponding slot in the outer pistion. The sleeve in turn is helically grooved on its exterior surface to accommodate a pin joined to a finger grip structure. In this manner, the collar is rotatable to advance or retract the inner piston relative to the outer piston and the finger grip structure, so that a selected pressure can be maintained without manual gripping of the inflator.

It is an object of the present invention to provide an improved injector device having the capability of delivering fluid at different pressure levels.

It is another object of the present invention to provide an inflation device for balloon angioplasty, which has the capability of delivering pressurizing fluid at different pressure levels, and which features "quick-release" locking means for selectively holding and releasing selected pressures in the fluid delivered by the inflation device.

Other objects and advantages of the invention will be more fully apparent from the ensuing disclosure and appended claims.

SUMMARY OF THE INVENTION

In one aspect, the present invention relates to a multi-pressure injector device, comprising:

an outer barrel attachable at a distal end thereof to a catheter or other fluid delivery means, and having at its proximal end laterally outwardly extending manual gripping means, the outer barrel enclosing an interior volume fillable with a selected fluid;

an inner barrel/plunger longitudinally slidable in the outer barrel, the inner barrel/plunger having (i) an interior volume in open flow communication with the interior volume of the outer barrel, and (ii) at its proximal end, second laterally outwardly extending manual gripping means;

a second plunger longitudinally slidable in the inner barrel/plunger;

wherein:

the second plunger and the inner barrel/plunger are independently translatable relative to one another;

the inner barrel/plunger and the outer barrel comprise locking means for selectively longitudinally locking the inner barrel/plunger and outer barrel relative to one another within the outer barrel, to preclude longitudinal translation therebetween, the inner barrel/plunger and outer barrel being selectively longitudinally lockable relative to one another along substantially the entire length of travel of the inner barrel/plunger in the outer barrel; and the second plunger is longitudinally slidable in the inner barrel/plunger while the inner barrel/plunger and outer barrel are longitudinally locked relative to one another by said locking means.

In another aspect, the present invention relates to an injector device of the above-described type, wherein the inner barrel/plunger comprises on an exterior surface thereof a track portion extending along substantially the entire length of the exterior surface, and wherein the outer barrel comprises on an inner surface thereof, along a proximal portion of the interior surface, a track portion which is complementarily configured relative to the track portion on the outer wall of the inner barrel/plunger, for mating therewith, when the respective tracks on the outer barrel inner surface and inner barrel/plunger outer surface are brought into engagement with one another.

In a further aspect of the invention as broadly claimed hereinabove, the second plunger is selectively lockable in a fixed position when it is fully distally extended to a maximum distal position in the inner barrel/plunger.

In a still further aspect of the invention as broadly described hereinabove, the locking means for selectively longitudinally locking the inner barrel/plunger and outer barrel relative to one another, are part of a locking assembly further comprising quick-release means for selectively engaging and disengaging the locking means, the quick-release means being manually actuatable.

The present invention in another aspect relates to an injector device as broadly described hereinabove, further comprising pressure indicating means joined in pressure indicating flow relationship with the interior volume of the outer barrel.

In another aspect, the present invention relates to an injector device as broadly claimed hereinabove, comprising a rotatable connector mounted at the distal end of the barrel, the rotatable connector comprising: a distal threaded neck portion, and a proximal collar portion of greater diameter than the barrel and receiving a distal portion of the barrel therein.

Other aspects and features of the present invention will be more fully apparent from the ensuing disclosure and appended claims.

BRIEF DESCRIPTION OF THE DRAWINGS

FIG. 3 is a top plan view of the injector device of FIGS. 1 and 2.

FIG. 4 is a bottom plan view of the injector device of FIGS. 1-3.

FIG. 5 is a side elevation view of the injector device of FIGS. 1-4, showing the inner barrel/plunger in proximally retracted position.

FIG. 6 is a side elevation view of the injector device of FIG. 5, axially rotated by 90° relative to the position shown in FIG. 5.

FIG. 7 is a side elevation view of the injector device of FIGS. 1-6, showing the second plunger fully proximally retracted.

FIG. 8 is a side elevation view of the injector device of FIG. 7, axially rotated by 90° relative to the position shown in FIG. 7.

FIG. 9 is a side elevation view of the inner second plunger element of the FIGS. 1-8 injector device, shown apart from the remaining injector device structure.

FIG. 10 is a side elevation view of the FIG. 9 second plunger, axially rotated by 90° from the position shown in FIG. 9.

FIG. 11 is a top plan view of the second plunger of FIGS. 9-10.

FIG. 12 is a bottom plan view of the second plunger of FIGS. 9-11.

FIG. 13 is a top plan view of the injector device of FIGS. 1-8, without the second plunger.

FIG. 14 is a cross-sectional elevation view of a rotatable connector assembly which may be usefully employed in the injector device of the present invention, in one embodiment thereof.

FIG. 15 is a cross-sectional elevation view of a rotatable connector which may be usefully employed on the injector device of the present invention, in another embodiment thereof.

FIG. 16 is a side elevation view of an endoflator device according to one embodiment of the present invention.

FIG. 17 is a side elevation view of a portion of the FIG. 15 endoflator device, showing the details of construction of the distal portion of the outer barrel thereof.

FIG. 18 is a perspective view of a portion of an injector device according to the present invention, showing the quick-lock/release structure thereof.

FIG. 19 is a top plan view of the quick-lock/release structure of FIG. 16, in closed (locked) position.

FIG. 20 is a top plan view of the quick-lock/release structure corresponding to FIG. 17, but showing the structure in open (released) position.

DETAILED DESCRIPTION OF THE INVENTION, AND PREFERRED EMBODIMENTS THEREOF

FIGS. 1-8 and 13 show a multi-pressure injection syringe according to one embodiment of the present invention. Each of these figures is numbered correspondingly with the others. FIGS. 9-12 show various views of the second plunger of the syringe of FIGS. 1-8, and the drawings of the plunger alone are likewise numbered correspondingly to FIGS. 1-8. FIG. 13 is a top plan view of the syringe of FIGS. 1-8, without the second plunger.

Figure 1:
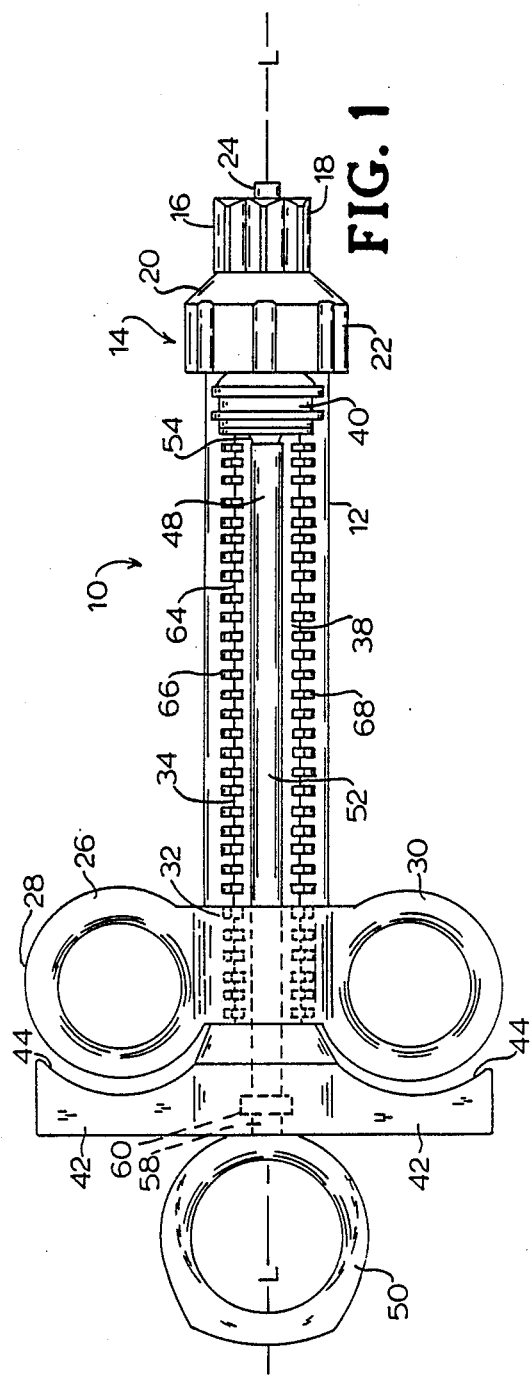
FIG. 1 is a side elevation view of an injector device according to one embodiment of the present invention.
Figure 2:
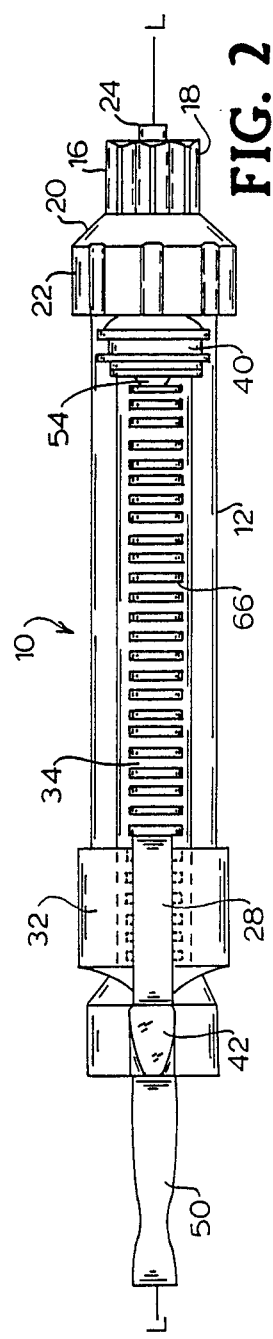
FIG. 2 is a side elevation view of the injector device FIG. 1, axially rotated by 90° relative to the position shown in FIG. 1.

Referring now to FIGS. 1 and 2, there are shown respective side elevation views of a dual-pressure injection syringe according to one embodiment of the invention. The syringe views in FIGS. 1 and 2 are axially rotated 90° relative to one another.

The illustrated syringe 10 comprises an outer barrel 12 attachable at a distal end 14 thereof to a catheter or other fluid delivery means (not shown for clarity) by the rotatable connector 16, as hereinafter described in fuller detail.

The rotatable connector 16 is mounted at a distal end of the syringe, and comprises a distal threaded neck portion 18, a frustoconical transition portion 20, and a proximal collar portion 22 which is of greater diameter than the barrel 12, and receives a distal portion of the barrel therein.

The threaded neck portion 18, frustoconical section 20, and proximal collar portion 22, may be integrally formed, or alternatively may be constructed of separate and distinct elements which are secured or affixed to one another in any suitable manner to form the rotatable connector.

The distal neck portion 18 of the rotatable connector may suitably comprise a luer connection structure as shown, in which the neck portion 18 annularly surrounding the discharge tube 24, is threaded on its interior surface, to receive a complementarily threaded male connector element.

Alternatively, the rotatable connector may be configured at its neck portion in any suitable manner for attachment or coupling to a catheter, or other fluid delivery means, such as a fluid injection manifold.

The outer barrel 12 is provided at its proximal end with laterally outwardly extending manual gripping means 26, comprising diametrally oppositely extending finger handles 28 and 30, each of which is of substantially circular shape as shown.

The finger handles 28 and 30 are secured to the barrel by means of a collar 32, with which the finger grips are integrally formed, the collar 32 being of generally cylindrical shape and interiorly configured to allow it to closely overfit the proximal end of the barrel. Thus, the collar 32 and distal end of the barrel 12 may be adhesively bonded, or press-fitted, or otherwise secured to one another in any suitable manner. It is within the purview of the invention to alternatively integrally form the barrel, collar 32, and finger grips 28 and 30, as a single piece. Further, the finger grips 28 and 30 may be configured in any other suitable shape other than the substantially circular form illustratively shown, however such substantially circular shape has been found to provide readily controllable manual manipulation of the syringe, without undue risk of fingers slipping from their intended grip positions.

The outer barrel encloses an interior volume which is fillable with a selected fluid, such as a contrast medium for angiographic applications, or an inflation fluid for endoflator applications. An inner barrel/plunger 34 is reposed in the interior volume of the outer barrel and is longitudinally slidable therein. The inner barrel/plunger has an interior volume in open flow communication with the interior volume of the outer barrel, by means of the central axial passage 38 entending through the inner barrel/plunger, including the piston 40 at the distal end of the inner barrel/plunger.

At its proximal portion, the inner barrel/plunger features laterally outwardly extending manual gripping means 42 which are configured on their frontal (distal) extremities with arcuate surfaces 44 accommodating gripping by a user's fingers, to assist in proximally retracting the inner barrel/plunger 34.

By the configuration shown, the laterally outwardly extending manual gripping means on the outer barrel, i.e., finger grips 28 and 30, are configured to proximally mate with the second laterally outwardly extending manual gripping means on the inner barrel/plunger, when the inner barrel/plunger is advanced in the outer barrel to its forwardmost, or distally maximum, extent. Thus the arcuate surfaces 44 effectively nest with the circular finger grips 28 and 30 when the inner barrel/plunger is in its fully forwardly advanced position.

A second plunger 48 is longitudinally slidable in the inner barrel/plunger 34. The second plunger suitably comprises at a proximal end thereof a thumb handle 50 which suitably may be of substantially circular shape, as shown. While other thumb handle or gripping structures may be employed, the circular shape shown has been found to afford good control of the syringe during use thereof, without undue risk of thumb slippage from its desired position when manipulating the second plunger.

The second plunger itself is more fully shown in FIGS. 9-12 hereof, as comprising a shaft 52 having a rubber stopper-type piston 54 mounted at the distal end thereof. The shaft 52 may comprise a proximal threaded end 56 which is mated with a complementarily threaded interior surface of the thumb grip 50. The thumb grip as shown comprises a cylindrical shaped shank segment 58 and a laterally outwardly extending flange member 60.

As used herein, the term "laterally" refers to the transverse direction relative to the central cylindrical axis of the syringe and/or its outer barrel, inner barrel/plunger, or second plunger components, as pertinent. The terms "axially" and "longitudinally" thus refer to the distance or direction of movement along the central cylindrical axis L—L of the syringe as illustratively shown in FIG. 1.

In the syringe of the present invention, as illustratively described hereinabove, the second plunger 48 and the inner barrel/plunger 34 are independently longitudinally translatable relative to one another. The inner barrel/plunger and the outer barrel comprise locking means for selectively longitudinally locking the inner barrel/plunger and outer barrel relative to one another within the outer barrel, to preclude longitudinal translation therebetween. The inner barrel/plunger and outer barrel are selectively longitudinally lockable relative to one another along substantially the entire length of travel of the inner barrel/plunger in the outer barrel.

With regard to the aformentioned locking structure, the inner barrel/plunger 34 comprises on an exterior surface 64 thereof diametrally opposed track portions 66 and 68, extending along substantially the entire length of the exterior surface. As used herein, the term phrase "diametrally opposed" means that the specified structures are transversely spaced apart from one another on the specified structure. Thus, in the embodiment shown, the respective track portions 66 and 68 each have a circumferential extent, or arc length, of about 90°, and are separated by a pair of diametrally opposed smooth outer surface segments 70 and 72.

The respective track portions 66 and 68 are formed as an array of longitudinally regularly spaced-apart, circumferentially extending ridges, wherein each of the ridges is preferably of the same size and shape characteristics as the others forming the track structure.

As indicated, the diametrally opposed track portions 66 and 68 extend along substantially the entire length of the exterior surface of the inner barrel/plunger. The complementary locking structure associated with the outer barrel of the syringe comprises on an inner surface of the outer barrel, along a proximal portion thereof, a track portion which is correspondingly and complementarily configured relative to the track portions on the outer surface of the inner barrel/plunger, and matable therewith, when one of the tracks on the inner barrel/plunger outer surface and the track on the outer barrel inner proximal surface are brought into engagement with one another.

The proximal inner surface of the outer barrel may feature only a single track portion, or, alternatively, two diametrally oppposed track portions may be provided on the outer barrel proximal inner surface. The arc length, or circumferential extent, of the outer barrel proximal inner surface track portion is preferably no greater than the circumferential extent of the complementary track portions on the inner barrel/plunger, and may be substantially less, it being necessary only to provide sufficient engagement with the track portion of the inner barrel/plunger in order to provide positive locking of the respective inner and outer barrels, to prevent longitudinal sliding movement of these elements relative to one another.

By way of illustration, the track portions on the outer surface of the inner barrel/plunger may each have a circumferential extent of about 90°, with the track portions on the inner wall of the outer barrel being of corresponding circumferential extent, whereby the track portions on the outer surface of the inner barrel/plunger may be selectively engaged with or disengaged from the track portions on the inner wall of the outer barrel, by selective rotation of the inner barrel/plunger relative to the outer barrel, such that when the respective track portions on the inner barrel/plunger and outer barrel are not in engagement, the inner barrel/plunger is freely longitudinally slidable in the outer barrel.

The inner barrel/plunger is prevented from being removed from the outer barrel by means of the distal flange 80 which is of corresponding height to the ridges forming the track portions 66 and 68, so that the complementary track portion on the inner surface of the outer barrel acts as a positive stop when the inner barrel/plunger is proximally retracted to its maximum proximal extent, where the circumferential flange 80 is in abutting contact with the forwardmost ridge of the outer barrel inner surface track portion.

Thus, when the syringe is in the position shown in FIG. 1, the inner barrel/plunger 34 may be freely slidingly longitudinally retracted relative to the outer barrel 12, but when the inner barrel/plunger is rotated 90° relative to the outer barrel, from the position shown in FIG. 1, the respective track portions on the outer barrel inner surface and the inner barrel outer surface are in engagement, and the inner barrel plunger, being locked, cannot be longitudinally translated relative to the outer barrel.

The second plunger 48 of the syringe is longitudinally slidable in the inner barrel/plunger 34 while the inner barrel/plunger and outer barrel are longitudinally locked relative to one another by the locking means. Thus, referring to FIG. 1, if the inner barrel/plunger 34 is rotated 90° from the position shown, while the second plunger 48 is retained in the same position as shown in FIG. 1, so that the respective finger grips 28 and 30 and thumb grip 48 are generally coplanar with one another, as shown in the FIG. 1 illustration, then the inner barrel/plunger is longitudinally locked relative to the outer barrel, while the second plunger is freely longitudinally slidable in the central longitudinal passage 38 of the inner barrel/plunger.

As previously described, the second plunger (see FIGS. 9–12) features a laterally outwardly extending flange member 60 constituting a part of the means for selectively locking the second plunger in a fixed position when the second plunger is fully distally extended in the inner barrel/plunger.

The complementary portion of the second plunger locking structure is associated with the proximal end of the inner barrel/plunger, and is illustrated in the top plan view of the inner barrel/plunger shown in FIG. 13. As shown by this drawing the proximal end of the inner barrel/plunger comprises a slotted opening 82 through which the flange member 60 is able to pass when aligned therewith upon translation of the second plunger to its maximum distal extent in the inner barrel/plunger. The inner barrel/plunger distally of the slot but in proximity thereto comprises an interior plenum 84 allowing free rotation of the second plunger flange member 60 therein subsequent to passage of the flange member through the slot opening 82. In this fashion, the second plunger may be selectively locked in position with a flange member in the plenum space 84, or the second plunger may be selectively disengaged from such locked position by rotation of the second plunger relative to the inner barrel/plunger, i.e., by axially rotating the second plunger until the flange member 60 is in register with slotted opening 82.

Accordingly, if the syringe is reposed in the position shown in FIG. 1, the second plunger is locked against longitudinal movement relative to the inner barrel/plunger 34, but may be retracted from the inner barrel/plunger by rotation of the second plunger by 90° relative to the position shown in FIG. 1, at which point the flange member of the second plunger is in register with the slotted opening at the proximal end of inner barrel/plunger 34.

It will be appreciated from the foregoing that the syringe construction of the present invention is extremely versatile, permitting the second plunger to be employed independently of the inner barrel/plunger.

The respective outer barrel, rotatable connector, finger grip structure, inner barrel/plunger, and second plunger components may be formed of any suitable materials of construction, as for example glass, plastic, or other suitable materials. Preferred plastics material of construction include polycarbonate and polypropylene for the outer barrel, rotatable connector, and finger grips, as well as the inner barrel/plunger and second plunger thumb grip, shank, and flange member, with the main shaft of the second plunger preferably being of nylon. The respective pistons 40 and 54 of the inner barrel/plunger and second plunger are suitably formed of a flexible resilient material, preferably an elastomeric material which provides fluid-tight sealing of the respective fluid volumes being longitudinally displaced by the respective pistons.

In an illustrative embodiment, having potential utility for angiography applications, the outer barrel of the syringe encloses an interior volume of approximately 15 cc, while the central longitudinal passage 38 of the inner barrel/plunger provides a fluid volume of approximately 3 cc, with the fluid volume in the interior passage of the inner barrel/plunger being fillable from the larger volume enclosed by the outer barrel of the syringe. By this construction, the outer barrel and inner barrel/plunger may be employed for injection applications where moderate injection pressures on the order of approximately 100 psi, and larger fluid volumes, are required. When higher injection pressures are necessary, the user can employ the second plunger and, by applying the same force as on the inner barrel/plunger for low pressure injection, dramatically increased injection pressures on the order of 500–600 psi can be attained.

It will be appreciated that the volumetric capacity and dimensional characteristics of the respective volumes inside the inner and outer barrels of the syringe of the present invention may be widely varied, depending on the specific required pressures and the type and character of the end use applications for which the syringe is intended. For angiographic and balloon angioplasty applications, it generally is satisfactory, where the interior volumes of the respective outer barrel and inner barrel/plunger are of generally cylindrical shape, to employ a ratio of the inner diameter of the outer barrel, to the inner diameter of the inner barrel/plunger (i.e., the diameter of the central longitudinal passage 38 as shown in the drawings), of from about 1.3 to about 3.0, and preferably from about 1.5 to about 2.2, and most preferably substantially about 2.0.

In use, the syringe may be filled, in the large volume enclosed by the outer barrel, by retracting the inner barrel/plunger to a desired extent, following which the fluid may be discharged from the syringe by relative forward movement of the inner barrel/plunger in the outer barrel. It may also be desirable to fill the outer barrel to a predetermined extent, and then to withdraw fluid from the outer barrel into the central longitudinal passage of the inner barrel/plunger, by longitudinally retracting the second plunger relative to the inner barrel/plunger, following which the fluid can be discharged at either low pressure or high pressure, by forwardly translating the inner barrel/plunger, or the second plunger, respectively. Alternatively, it may be desirable in some instances to maintain the inner barrel/plunger in fully distally extended position, and to fill only the central longitudinal passage of the inner barrel/plunger, by proximally retracting the second plunger, following which the fluid taken into the central passage may be discharged at high pressure by forwardly translating the second plunger relative to the inner barrel/plunger.

FIG. 14 shows a cross-sectional elevational view of a rotatable connector suitable for use with the syringe of the present invention. The connector illustrated in this drawing is shown with a corresponding distal portion of the outer barrel 110 of the syringe.

As illustrated, the outer barrel of the syringe comprises a transverse end wall 112 which extends annularly between the cylindrical side walls 114 of the outer barrel 110, and a distal projection portion 116 of the outer barrel. The distal projection portion 116 has bonded thereto a discharge section 118, whose distal end section 122 is of enlarged cross-section relative to the intermediate section 120. The enlarged end section 122 is disposed in a cavity 124 of the rotator housing 126. A fluid flow passage 128 extends through the discharge section 118, and communicates with a correspondingly axially aligned fluid discharge passage 130 in rotator housing 126.

Intermediate the discharge section 118 and distal projection portion 116 are an O-ring 132, and an annular retaining ring 134 which is bonded at its outer circumference to the rotator housing. Such bonding may be effected in any suitable manner, as for example ultrasonic welding, solvent bonding, adhesive attachment, etc.

The discharge passage 130 in the rotator housing is defined by the tubular extension 136 thereof, surrounding which is an annular cavity 138 accommodating the insertion and attachment of a male threaded fitting, securement being effected by means of the threading 140 on the inner surface bounding the cavity, such that the rotator housing thereby provides a female luer coupling. The rotator housing 126 thus forms the distal threaded neck portion of a rotatable connector 142, which further comprises the frustoconical transition section 144 and the proximal collar section 146.

The exterior surface of the proximal collar portion 146 of the rotatable connector 142 may suitably be grooved, knurled, or otherwise textured or configured to provide a slipresistant surface structure, for manual gripping and rotation of the rotatable connector.

In this respect, it is to be noted that the proximal collar portion of the rotatable connector is of greater diameter than the barrel 110 of the syringe, with the proximal collar portion receiving a distal portion of the barrel, as illustrated.

The provision of a distal collar portion of greater diameter than the barrel of the syringe enables ready manual grasping of the rotatable connector, facilitating the connection thereof to the associated fitting of the catheter or other fluid flow structure. To my knowledge, all prior art connectors for syringes have been of smaller diameter than the syringe barrel, which has rendered it highly difficult in many instances to properly align and join the syringe connector fitting to the complementarily configured matable structure for attachment thereto. Accordingly, the provision of a rotatable connector having a manually grippable collar of the character described, is a substantial advance in the syringe art, which substantially enhances the ease of use of syringes which are coupled to other fluid delivery structures.

FIG. 15 is a cross-sectional, elevational view of a rotatable connector according to another embodiment of the invention. In this alternative rotatable connector embodiment, the rotatable connector 200 comprises a unitary connector body 202 comprising a threaded neck portion 204, a frustoconical transition portion 206, and a proximal collar portion 208, wherein the proximal collar portion is of greater diametral extent than the syringe barrel 210, and is adapted to receive a distal portion of the barrel, in closely fitting fashion. For this purpose, the syringe barrel comprises a main cylindrical body portion having a cylindrical enclosing wall 212, to which a tapered neck section 214, of smaller diameter than the main body portion of the outer barrel, is joined by the frustoconical transition section 216. The outer extremity 218 of frustoconical transition section 216 extends radially outwardly beyond the cylindrical enclosing wall 212, to form a radial protrusion at the shoulder between transition section 216 and the cylindrical wall 212.

The proximal collar portion 208 of the rotatable connector is configured with an inner circumferentially extending groove 220, into which the shoulder protrusion 218 is received, to retain the rotatable connector against axial movement relative to the barrel 210.

The neck section 214 of the barrel has in proximity to its distal extremity a circumferentially extending groove 222 cooperatively mating with the circumferential protrusion 224 on the rotatable coupling.

Thus, the rotatable coupling is formed as a single piece fitting, comprising an interior locking structure which is snap-fittingly mountable on the neck section of the outer barrel, with the locking structure 224 of the rotatable connector being received in the circumferential groove 222 of the neck section, and retained therein against longitudinal movement of the rotatable connector relative to the outer barrel, yet allowing free circumferential rotatation of the rotatable connector relative to the barrel.

At its distal portion, the neck 204 of the rotatable coupling is provided with threading 230 on an interior surface bounding the annular cavity 232. At its central portion cavity 232 is bounded by the annular discharge nozzle 234 having therein a central axially extending passageway 236 communicating with the axially extending passageway 238 within the tapered neck section 214 of the syringe barrel.

The rotatable connector embodiment of FIG. 15, in its provision of a snap-fitting structure, eliminates the bonding operation which is necessary to form the rotatable connector in the embodiment shown in FIG. 14.

FIG. 16 shows an alternative embodiment of the invention wherein a syringe of the general type shown in FIG. 1 is adapted for use as an endoflator, or inflation device, for balloon angioplasty applications. Such inflator device may be employed to inflate the angioplasty balloon or expander member reposed at the end of an angioplasty catheter, or to deliver a contrast medium through a catheter in the previously described manner.

The FIG. 16 inflation device has been numbered correspondingly with respect to FIG. 1, the same reference numerals identifying the same elements of the device.

The inflator device of FIG. 16 has been modified, however, relative to the FIG. 1 apparatus, in the provision of a pressure indicating means 300, which may comprise an analog pressure transducer, having a needle indicator 301 constructed and arranged to indicate a numerical pressure value in suitable units such as bars, atmospheres, pounds per square inch, or kilograms per square centimeter.

FIG. 17 is a side view of the FIG. 16 apparatus, axially rotated by 90° relative to the position of the device as shown in FIG. 16. As shown in this drawing, the pressure indicating means 300 is coupled to the interior volume of the outer barrel, at the distal end thereof, by means of pressure sensing conduit 302, which is connected at one end to the inner volume of the outer barrel by means of a suitable passage or opening in the outer barrel wall, with the other end of the pressure sensing conduit being joined to the pressure indicating means, for operation of such indicating means in a known manner, to indicate the pressure of the fluid being delivered by the inflation device. In order that the operation of the pressure indicating means is not precluded by the maximum distal positioning of the maximum distal positioning of the piston mounted on the inner barrel/plunger 34, the outer barrel is provided on its interior surface with a circumferentially extending annular stop ring 304, which provides a stop element for the inner barrel/plunger piston, so that the pressure sensing conduit 302 is always in open flow communication with the fluid contents of the syringe being dispensed, to thereby provide a continuous readout of the pressure of fluid dispensed by the inflator device.

It will be appreciated that in lieu of the specific analog pressure indicating means illustratively described, digital readout means may alternatively or additionally be provided, depending on the needs and preferences of the end user of the inflator device.

FIG. 18 shows a perspective view of a syringe adapted for use as an inflation device.

The inflation device 400 comprises an outer barrel 402, to the distal end of which is attached a rotatable coupler 404, which may for example be of the type described hereinabove in connection with FIGS. 14 or 15. The outer barrel 402 is integrally formed with a proximal manual gripping structure 406 comprising finger grips 408 and 410. Slidably received with the outer barrel 402 is the inner barrel/plunger 412 having diametrally opposed longitudinal extending track portions 414 and 416 on its outer surface, separated by surface portions 418 which are devoid of the track structure.

Mounted on the exterior surface of the outer barrel 402 is a quick-lock/release annular ring 420 which is selectively rotatable between "RELEASE" and "LOCK" positions as shown, the position being indicated by an indicator bar 422 radially protruding from the ring 420 and adapted for engagement with engagment with a thumb or finger of the user to selectively lock or release the inner barrel/plunger against longitudinal movement relative to the outer barrel 402, in a quick-release fashion.

Figure 21:
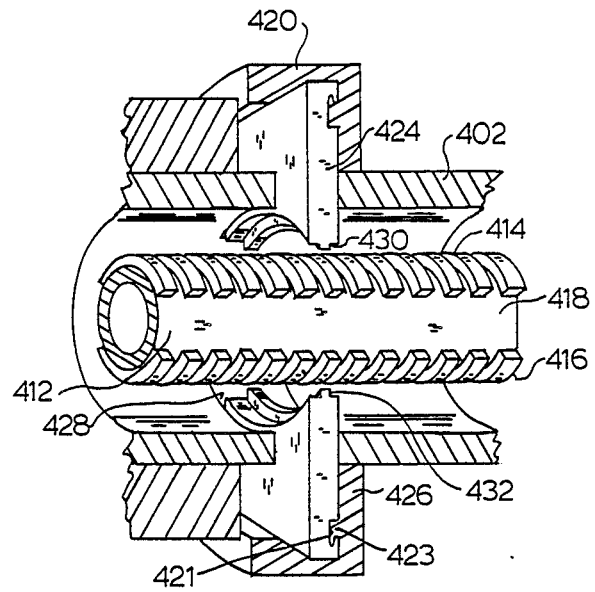
FIG. 21 is a perspective cut-away view of the quick-lock/release structure of FIGS. 16-17.

As shown in the respective plan views of FIGS. 19 and 20 and the perspective view of FIG. 21, the ring 420 features circumferentially extending protrusions 423 which engage correspondingly configured grooves 421 on the diametrally opposed locking elements 424 and 426, which extend from the ring radially inwardly through slots 428 in the outer barrel 402, extending partially radially into the interior volume of the outer barrel toward the inner barrel/plunger 412. Each of the radially extending locking elements 424 and 429 has on its radially innermost surface a track configration which is complementary to the track portions 414 and 416 of the inner barrel/plunger.

The ring protrusions 423 and corresponding locking element grooves 421 define arcuate paths of engagement which are of radially varying position, as indicated by the dotted lines shown in the plan views of FIGS. 19 and 20, as demarcating the general locus of engagement between the ring protrusions and locking element grooves. It therefore will be apparent that the locking elements 424 and 426 are lockingly coupled with one another, so that the locking elements can move radially inwardly or radially outwardly, depending on the direction of rotation of the ring.

Thus, when the quick-lock/release ring is selectively manually placed in the "LOCK" position, the track surfaces 430 and 432 of the respective radial locking elements 424 and 426 engage the respective track portions 414 and 416 of the inner barrel/plunger 412. When the quick-lock release ring is manually rotated to the "RELEASE" position, the track surfaces 430 and 432 are disengaged from the track portions 414 and 416 of the inner barrel/syringe, and the inner barrel/plunger then may move freely longitudinally relative to the outer barrel 402. In this fashion, a quick-lock/release structure is provided which is manually actuatable by simple lateral adjustment with the user's finger or thumb, so that a selected pressure level, associated with a specific longitudinal position of the inner barrel/plunger relative to the outer barrel, can be maintained by placing the retaining ring into the "LOCK" position, and then quickly released to minimize balloon deflation times in the balloon angioplasty procedure.

When the locking elements 424 and 426 engage the respective track portions 414 and 416 of the inner barrel/plunger 412, the inner barrel/plunger is lockingly retained against longitudinal movement relative to the outer barrel. In some instances, it may be desirable to adjust the longitudinal position of the plunger to a relatively slight degree, and in such instances, it may be advantageous to provide the track portions on the inner barrel/plunger with a threaded configuration, such that when the quick-lock/release ring is in the locked position, the inner barrel/plunger can still be advanced or retracted, by appropriate rotation of the inner barrel/plunger relative to the outer barrel. Such arrangement thus permits "fine tuning" adjustment of the presssure, once the inflator device is placed in the "LOCK" position.

While the quick-lock/release structure has been shown and described as comprising two diametrally opposed locking elements having track surfaces on their radially innermost extremities, it will be appreciated that the locking structure may alternatively comprise only one such locking element, or alternatively, more than two, as may be necessary or desirable for a given end use application.

While not specifically shown in FIG. 18, the inflation device therein illustrated may suitably comprise a pressure indicating means of the type shown and described in connection with FIGS. 16 and 17 herein.

Although the invention has been described herein with reference to embodiments utilizing a dual barrel and plunger strucure, it will be recognized that it is within the purview of the invention to provide multiple barrel and plunger structures, having three or more barrels and plungers.

Further, while the invention has been illustrated with reference to specific embodiments, it will be apparent that numerous variations, modifications, and embodiments are possible, and all such apparent variations, modifications, and embodiments are to be regarded as being within the spirit and scope of the invention.

What is claimed is:

1. A multi-pressure injector device, comprising:
   an outer barrel attachable at a distal end thereof to a catheter or other fluid delivery means, and having at its proximal end laterally outwardly extending manual gripping means, the outer barrel enclosing an interior volume fillable with a selected fluid;
   an inner barrel/plunger longitudinally slidable in the outer barrel, the inner barrel/plunger having (i) an interior volume in open flow communications with the interior volume of the outer barrel, and (ii) at its proximal end, second laterally outwardly extending manual gripping means; and
   a second plunger longitudinally slidable in the inner barrel;
   wherein:
   the second plunger and the inner barrel/plunger are independently translatable relative to one another;
   the inner barrel/plunger and the outer barrel comprise locking means for selectively longitudinally locking the inner barrel/plunger and outer barrel relative to one another within the outer barrel, to preclude longitudinal translation therebetween, the inner barrel/plunger and outer barrel being selectively longitudinally lockable relative to one another along substantially the entire length of travel of the inner barrel/plunger in the outer barrel;
   the second plunger is longitudinally slidable in the inner barrel/plunger while the inner barrel/plunger and outer barrel are locked relative to one another by said locking means;
   the inner locking means is characterized in that the inner barrel/plunger comprises on an exterior surface thereof a track portion extending along substantially the entire length of the exterior surface, and wherein the outer barrel comprises, on an inner surface thereof, along a proximal portion of the interior surface, a track portion which is complementarily configured relative to the track portion on the outer wall of the inner barrel/plunger, for mating therewith, when the respective tracks on the outer barrel inner surface and inner barrel/plunger outer surface are brought into engagement with one another; and
   the track portion on the outer surface of the inner barrel/plunger may be selectively engaged with or disengaged from the track portion on the inner wall of the outer barrel, by selective rotation of the inner barrel/plunger relative to the outer barrel, such that when the respective track portions on the inner barrel/plunger and outer barrel are not in engagement, the inner barrel/plunger is freely longitudinally slidable in the outer barrel.

2. A device according to claim 1, wherein the laterally outwardly extending manual gripping means on the outer barrel is configured to proximally mate with the second laterally outwardly extending manual gripping means, when the inner barrel/plunger is fully distally extended into the interior volume of the outer barrel.

3. A device according to claim 2, wherein the laterally outwardly extending manual gripping means at the proximal end of the outer barrel comprises diametrally oppositely extending finger handles, each of substantially circular shape.

4. A device according to claim 1, wherein the second plunger comprises at a proximal end thereof a thumb handle of substantially circular shape.

5. A device according to claim 1, wherein the second plunger is selectively lockable in a fixed position when it is fully distally extended in the inner barrel/plunger.

6. A device according to claim 5, wherein the second plunger has on its proximal portion a laterally outwardly extending flange member, and the proximal end of the inner barrel/plunger comprises a slotted opening through which the flange member is able to pass when aligned therewith upon proximal translation of the second plunger to its maximum proximal extent in the inner barrel/plunger, the inner barrel/plunger distally of the slot but in proximity thereto comprising an interior plenum allowing free rotation of the second plunger flange member therein subsequent to passage of the flange member through the slot opening, whereby the second plunger may be selectively locked in position with the flange member in the plenum space, or may be selectively disengaged from such locked position by rotation of the second plunger relative to the inner barrel/plunger.

7. A device according to claim 1, comprising a rotatable connector mounted at the distal end of the outer barrel, the rotatable connector comprising a distal threaded connector portion and a proximal collar portion, the proximal collar portion being of greater diameter than the outer barrel and receiving the outer barrel therein, whereby the outer surface of the collar portion of the rotatable connector provides a manually grippable surface for manual rotation of the rotatable connector to effect selectively coupling of the syringe to, or uncoupling of the syringe from, a catheter fitting or other structure couplable therewith.

8. A device according to claim 7, wherein the distal threaded portion of the rotatable coupling comprises a luer connection structure.

9. A device according to claim 7, wherein the distal threaded portion and proximal collar portion of the rotatable connector are integrally formed.

10. A device according to claim 8, wherein the distal end of the outer barrel comprises a tapered neck section of smaller diameter than a main body portion of the outer barrel, the neck section having in proximity to its distal extremity a circumferentially extending groove, and wherein the rotatable coupling is formed as a single piece fitting comprising interior locking structure which is snap-fittingly mountable on the neck section of the outer barrel, with the locking structure of the rotatable connector being received in the circumferential groove of the neck section and retained therein against longitudinal movement of the rotatable connector relative to the outer barrel, yet allowing free circumferential rotation of the rotatable connector relative to the outer barrel.

11. A device according to claim 1, wherein the interior volumes of the respective outer barrel and inner barrel/plunger are of generally cylindrical shape, and wherein the ratio of the inner diameter of the outer barrel, to the inner diameter of the inner barrel/plunger, is from about 1.3 to about 3.0.

12. A device according to claim 1, wherein the interior volumes of the respective outer barrel and inner barrel/plunger are of generally cylindrical shape, and wherein the ratio of the inner diameter of the outer barrel, to the inner diameter of the inner barrel/plunger, is from about 1.5 to about 2.2.

13. A device according to claim 1, wherein the interior volumes of the respective outer barrel and inner barrel/plunger are of generally cylindrical shape, and wherein the ratio of the inner diameter of the outer barrel, to the inner diameter of the inner barrel/plunger, is substantially about 2.0.

14. A device according to claim 1, wherein the inner barrel/plunger comprises at a distal extremity thereof a flexible resilient sealing element.

15. A device according to claim 1, wherein said locking means for selectively longitudinally locking the inner barrel/plunger and outer barrel relative to one another, are part of a locking assembly further comprising quick-release means for disengaging the locking means, the quick-release means being manually actuatable.

16. A device according to claim 1, further comprising pressure indicating means joined in pressure indicating flow relationship with the interior volume of the outer barrel.

17. A device according to claim 16, further comprising manually actuatable quick-release means associated with said locking means for selectively longitudinally locking the inner barrel/plunger and outer barrel relative to one another.

18. A device according to claim 16, wherein the pressure indicating means comprise an analog indicating element indicating the pressure of the fluid in the inner barrel of the syringe.

19. A device according to claim 16, wherein the pressure indicating means comprise a digital indicating means indicating the pressure of the fluid in the inner barrel of the syringe.

20. An injector device according to claim 1, comprising a rotatable connector mounted at the distal end of the syringe, the rotatable connector comprising: a distal threaded neck portion, and a proximal collar portion of greater diameter than the barrel and receiving a distal portion of the barrel therein.

21. A device according to claim 20, wherein the threaded neck portion and proximal collar portion are integrally formed.

22. A device according to claim 20, wherein the distal neck portion of the rotatable connector comprises a luer connection structure.

23. A device according to claim 20, wherein the distal end of the outer barrel comprises a tapered neck section of smaller diameter than a main body portion of the outer barrel, the neck section having in proximity to its distal extremity a circumferentially extending groove, and wherein the rotatable coupling is formed as a single piece fitting comprising interior locking structure which is snap-fittingly mountable on the neck section of the outer barrel, with the locking structure of the rotatable connector being received in the circumferential groove of the neck section and retained therein against longitudinal movement of the rotatable connector relative to the outer barrel, yet allowing free circumferential rotation of the rotatable connector relative to the outer barrel.

24. An inflation device, comprising:
a barrel having a distal end attachable to a catheter or other fluid delivery means, the barrel enclosing an interior volume fillable with a selected fluid;
a plunger longitudinally slidable in the barrel, with an external surface having a track portion thereon extending longitudinally along the plunger;
a slot in a proximal portion of the barrel, extending therethrough;
a locking and release structure comprising an annular ring mounted on the barrel on an external surface thereof and having a first engagement member extending along a circumferential path having a progressively varying radial position along its circumferential extent, a locking element comprising a second engagement member lockingly engageable with the first engagement member on the annular ring, said locking element extending through the slot in the barrel radially inwardly into the interior volume and having an engagement surface on a radially innermost portion thereof, operatively arranged so that (1) the locking element engagement surface engages the track portion on the plunger, when the ring is selectively positioned so that the locking element is directed radially inwardly to a maximum extent, and (2) the locking element is released from its locked position having the engagement surface thereof in engagement with the track portion on the plunger, when the ring is selectively rotated away from said selective position.

25. An inflation device according to claim 24, further comprising a central longitudinal passage in said plunger in open flow communication with the interior volume of the barrel, and a second plunger slidably reposed in said central longitudinal passage.

26. An inflation device according to claim 24, further comprising pressure indicating means operatively connected to the barrel and in open flow communication with the interior volume thereof, for monitoring the pressure of fluid in the interior volume.

* * * * *